(12) United States Patent
Shirotani et al.

(10) Patent No.: US 11,033,458 B2
(45) Date of Patent: Jun. 15, 2021

(54) BAG FOR LIQUIDS

(71) Applicant: HISAMITSU PHARMACEUTICAL CO., INC., Tosu (JP)

(72) Inventors: Yusuke Shirotani, Tsukuba (JP); Kazuki Kuriyama, Tsukuba (JP); Seiji Tokumoto, Tsukuba (JP)

(73) Assignee: HISAMITSU PHARMACEUTICAL CO., INC., Tosu (JP)

( * ) Notice: Subject to any disclaimer, the term of this patent is extended or adjusted under 35 U.S.C. 154(b) by 400 days.

(21) Appl. No.: 16/061,866

(22) PCT Filed: Dec. 1, 2016

(86) PCT No.: PCT/JP2016/085777
§ 371 (c)(1),
(2) Date: Oct. 22, 2018

(87) PCT Pub. No.: WO2017/104432
PCT Pub. Date: Jun. 22, 2017

(65) Prior Publication Data
US 2019/0117512 A1    Apr. 25, 2019

(30) Foreign Application Priority Data

Dec. 15, 2015   (JP) .............................. JP2015-243924

(51) Int. Cl.
*A61J 1/14*     (2006.01)
*A61J 1/10*     (2006.01)
(Continued)

(52) U.S. Cl.
CPC ............... *A61J 1/1475* (2013.01); *A61J 1/10* (2013.01); *A61M 5/14244* (2013.01);
(Continued)

(58) Field of Classification Search
CPC .... A61J 1/1474; A61J 1/10; A61J 1/16; A61J 1/1493; A61J 1/12; A61J 1/14;
(Continued)

(56) References Cited

U.S. PATENT DOCUMENTS 3,993,069 A * 11/1976 Buckles .................... A61J 1/05
604/132
5,693,018 A    12/1997 Kriesel et al.
(Continued)

FOREIGN PATENT DOCUMENTS

JP         1043295 A      2/1998
JP    2001104477 A      4/2001
(Continued)

OTHER PUBLICATIONS

Notice of Allowance dated Apr. 2, 2019 in corresponding Japanese application P2017-555973.
(Continued)

*Primary Examiner* — Bhisma Mehta
*Assistant Examiner* — John J Crawford
(74) *Attorney, Agent, or Firm* — Nath, Goldberg & Meyer; Joshua B. Goldberg

(57) ABSTRACT

A liquid bag according to one embodiment stores liquid containing an active ingredient to be transdermally administered. This liquid bag includes a bag body configured to store the liquid and feed the liquid toward an injection needle. The bag body includes a tubular portion. At least part of the tubular portion is bent with respect to the axial direction of the tubular portion with the liquid being stored in the tubular portion.

4 Claims, 8 Drawing Sheets

(51) Int. Cl.
*A61M 5/152* (2006.01)
*A61M 5/158* (2006.01)
*A61M 5/165* (2006.01)
*A61M 5/168* (2006.01)
*A61M 5/142* (2006.01)
*A61M 39/22* (2006.01)

(52) U.S. Cl.
CPC ............ *A61M 5/152* (2013.01); *A61M 5/158* (2013.01); *A61M 5/165* (2013.01); *A61M 5/16813* (2013.01); *A61M 39/223* (2013.01)

(58) Field of Classification Search
CPC .... A61J 1/202; A61M 5/14244; A61M 5/158; A61M 5/165; A61M 5/16813; A61M 39/223; A61M 5/145; A61M 2005/1416; A61M 5/152; A61M 5/1418; F04B 43/084
See application file for complete search history.

(56) References Cited

U.S. PATENT DOCUMENTS

| | | | |
|---|---|---|---|
| 2004/0007590 A1 | 1/2004 | Hedington et al. | |
| 2005/0277883 A1 | 12/2005 | Kriesel | |
| 2006/0100578 A1 | 5/2006 | Lieberman et al. | |
| 2007/0156103 A1* | 7/2007 | Chatlynne | A61M 5/152 604/257 |
| 2010/0234824 A1 | 9/2010 | Christoph et al. | |
| 2013/0138044 A1* | 5/2013 | Schuman | G09F 3/205 604/174 |
| 2013/0267930 A1* | 10/2013 | Robson | A61M 5/445 604/500 |
| 2014/0323969 A1* | 10/2014 | Young | A61M 5/44 604/113 |
| 2015/0190569 A1 | 7/2015 | Nagel et al. | |

FOREIGN PATENT DOCUMENTS

| | | |
|---|---|---|
| JP | 2002119586 A | 4/2002 |
| JP | 2006-280758 A | 10/2006 |
| JP | 2009148551 A | 7/2009 |
| JP | 2013540536 A | 11/2013 |
| JP | 2014111163 A | 6/2014 |
| JP | 2015521510 A | 7/2015 |
| WO | 2012054973 A1 | 5/2012 |

OTHER PUBLICATIONS

The Extended European Search Report dated Apr. 18, 2019 corresponding to application No. 16875415.8-1122.
International Preliminary Report on Patentability dated Jun. 28, 2018 corresponding to application No. PCT/JP2016/085777.
International Search Report dated Feb. 21, 2017 corresponding to application No. PCT/JP2016/085777.

* cited by examiner

BAG FOR LIQUIDS

This is a National Phase Application filed under 35 U.S.C. 371 as a national stage of PCT/JP2016/085777, filed Dec. 1, 2016, an application claiming the benefit of Japanese Application No. 2015-243924, filed Dec. 15, 2015, the content of each of which is hereby incorporated by reference in its entirety.

TECHNICAL FIELD

One aspect of the present invention relates to a liquid bag for storing liquid containing an active ingredient to be transdermally administered.

BACKGROUND ART

Liquid bags used for transdermal administration are conventionally known. For example, Patent Literature 1 describes a liquid-medicine continuous injection device including an elastic bag configured to be filled with liquid medicine and a case configured to accommodate the elastic bag, and the device is configured to cause the liquid medicine to continuously flow out by constricting force of the elastic bag. Patent Literature 2 describes a liquid administration device including an elastic bag configured to store liquid under a predetermined pressure.

CITATION LIST

Patent Literature

Patent Literature 1: JP 2001-104477 A
Patent Literature 2: U.S. Pat. No. 3,993,069

SUMMARY OF INVENTION

Technical Problem

In order to store an active ingredient in an amount needed to be transdermally administered in the elastic bag described in Patent Literature 1 or 2, the dimensions of the elastic bag need to be increased to a certain extent. However, increased dimensions will reduce portability. For example, in such a case, it is difficult to administer the active ingredient to a living body with a transdermal administration device that includes the bag and is attached to the living body. In view of this, a liquid bag that can store an active ingredient in an amount needed for transdermal administration and is excellent in portability is desired.

Solution to Problem

A liquid bag according to one aspect of the present invention is a liquid bag for storing liquid containing an active ingredient to be transdermally administered, and includes a bag body configured to store the liquid and feed the liquid toward an injection needle. The bag body includes a tubular portion, and at least part of the tubular portion is bent with respect to an axial direction of the tubular portion with the liquid being stored in the tubular portion.

In this aspect, because at least part of the tubular portion storing the liquid is bent, the tubular portion having a longer length can be accommodated in a limited space. Thus, a larger amount of liquid can be stored within the limited space. Forming the bag body in this manner allows the space occupied by the bag body to be narrowed, and thus the portability of the liquid bag can be enhanced and the active ingredient in an amount needed for transdermal administration can be stored in the liquid bag.

Advantageous Effects of Invention

According to one aspect of the present invention, the liquid bag that can store the active ingredient in an amount needed for transdermal administration and is excellent in portability can be provided.

DESCRIPTION OF EMBODIMENTS

An embodiment of the present invention will now be described in detail with reference to the attached drawings. In the description of the drawings, like or equivalent elements are designated by like reference signs, and duplicate description is omitted.

A configuration of a liquid bag according to the embodiment will be described with reference to FIGS. 1 to 6. The liquid bag is an article used for transdermal administration, and is more specifically an article configured to store liquid containing an active ingredient to be transdermally administered (hereinafter simply called "liquid"). The liquid (active ingredient) fed from the liquid bag is administered into a living body through an injection needle. The liquid bag according to the embodiment as a whole has characteristics of being flexible and thin, and thus is excellent in portability. The term "thin" herein means that the thickness of the liquid bag is small when the liquid bag is attached to the living body. The thickness of the liquid bag is a distance from a portion (lowermost portion) of the liquid bag that is closest to the living body to a portion (uppermost portion) of the liquid bag that is farthest from the living body. The term "portability" means ease for a person (user of an administration device), to whom the active ingredient is administered through the injection needle inserted into his/her skin, to be able to move while carrying the liquid bag.

Figure 1:
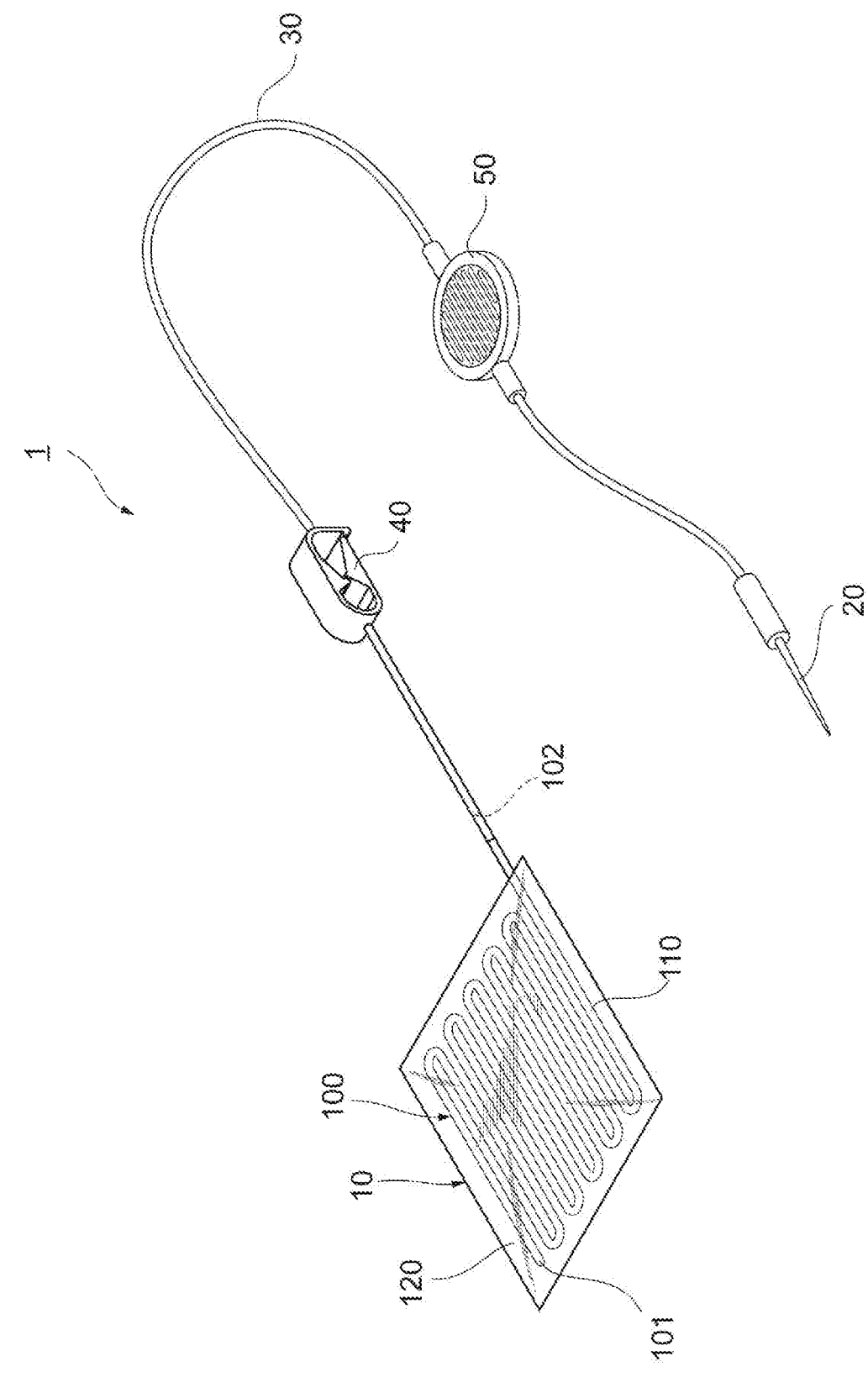
FIG. 1 is a diagram illustrating an example of an administration device including a liquid bag according to an embodiment.

FIG. 1 illustrates one example of an administration device 1 including this liquid bag 10 according to the present embodiment. The administration device 1 is a device configured to administer an active ingredient into a living body through a skin (i.e., configured to transdermally administer the active ingredient). In the example of FIG. 1, the administration device 1 includes the liquid bag 10, an injection needle 20, a long thin tube 30 connecting the liquid bag 10 and the injection needle, and a clamp 40 and a filter 50 both provided at some midpoints of the tube 30. However, the configuration of the administration device is not limited to this example. For example, the clamp 40 and the filter 50 are not indispensable components, and the administration device may include another component.

The liquid bag 10 includes a bag body 100 configured to store or be able to store liquid, and to feed the liquid toward the injection needle 20. As is understood, the bag body 100 has a bottom 101, and also has a port 102 for feeding liquid toward the injection needle. The port 102 may be used to charge liquid into the liquid bag 10 and, in this case, the port 102 serves as both an outlet and an inlet for the liquid. Alternatively, an outlet and an inlet may be formed separately in the bag body.

The bag body 100 has a tubular portion 110. The tubular portion 110 is a portion having a shape like a long thin tube. The tubular portion 110 is part or the whole of the bag body 100, and thus the tubular portion 110 serves as a storage for liquid. Thus, the tubular portion 110 is different from a tube (e.g., the tube 30 in FIG. 1) in which liquid flows in from one end and the liquid is discharged from the other end. In the present embodiment, the entire bag body 100 is the tubular portion 110. In this case, the liquid bag 10 can be considered to include the bag body 100 having a tubular shape.

Figure 2:
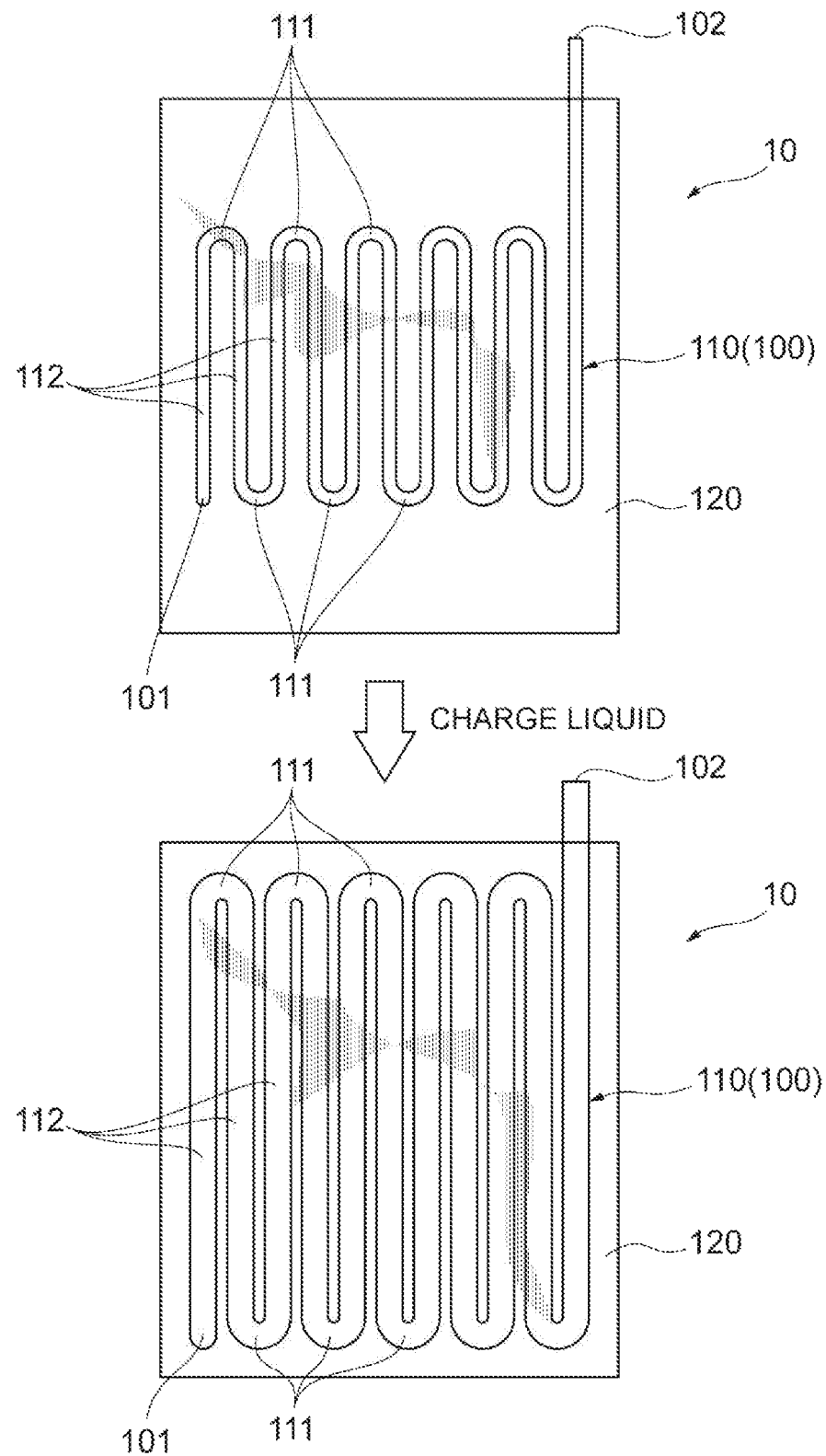
FIG. 2 is a diagram illustrating an example of change of a bag body when filling the empty bag body with liquid.

The bag body 100 (tubular portion 110) has flexibility. Thus, the bag body 100 (tubular portion 110) is expanded or extended by pressure of charged liquid, and stores (retains) the liquid. The bag body 100 (tubular portion 110) constricts due to its own tension, thereby discharging the stored liquid from the port 102. Examples of material of the bag body 100 (tubular portion 110) to obtain such characteristics include silicone rubber, natural rubber, and synthetic rubber. However, the material is not limited to particular one, and any material may be used if a bag body 100 (tubular portion 110) that can be easily bent can be made thereof. Due to the flexibility of the bag body 100 (tubular portion 110), the bag body 100 (tubular portion 110) can inflate when the bag body 100 is charged with liquid. As depicted in FIG. 2, by filling the bag body 100 with liquid, apparent dimensions (e.g., outside diameter and length) of the tubular portion 110 may increase. In the example of FIG. 2, if a plurality of straight portions (portions 112 described later) of the meandering bag body 100 (tubular portion 110) are each fixed, expansion of the tubular portion 110 in the radial direction thereof can be suppressed and the bag body 100 (tubular portion 110) can be extended in the axial direction of the tubular portion 110 when the bag body 100 (tubular portion 110) is expanded.

In a state in which liquid is stored in the tubular portion 110, at least part of the tubular portion 110 is bent with respect to the axial direction (longitudinal direction) of the tubular portion 110. Herein, the "state in which liquid is stored in the tubular portion" is a state in which liquid exists in at least part of the tubular portion, and conceptually includes a state in which the tubular portion is filled with liquid. The state in which the tubular portion is bent with respect to the axial direction (longitudinal direction) thereof is a state in which part of the tubular portion deviates from a straight line extending along the axial direction of the tubular portion. The state in which the tubular portion is bent with respect to the axial direction thereof means a state in which the flow passage of liquid is bent. The tubular portion 110 is bent at at least one location. By bending the tubular portion 110 in this manner, the tubular portion 110 having a certain length can be contained within a limited space or a limited form, which can contribute to the improvement of portability of the liquid bag 10.

Figure 3:
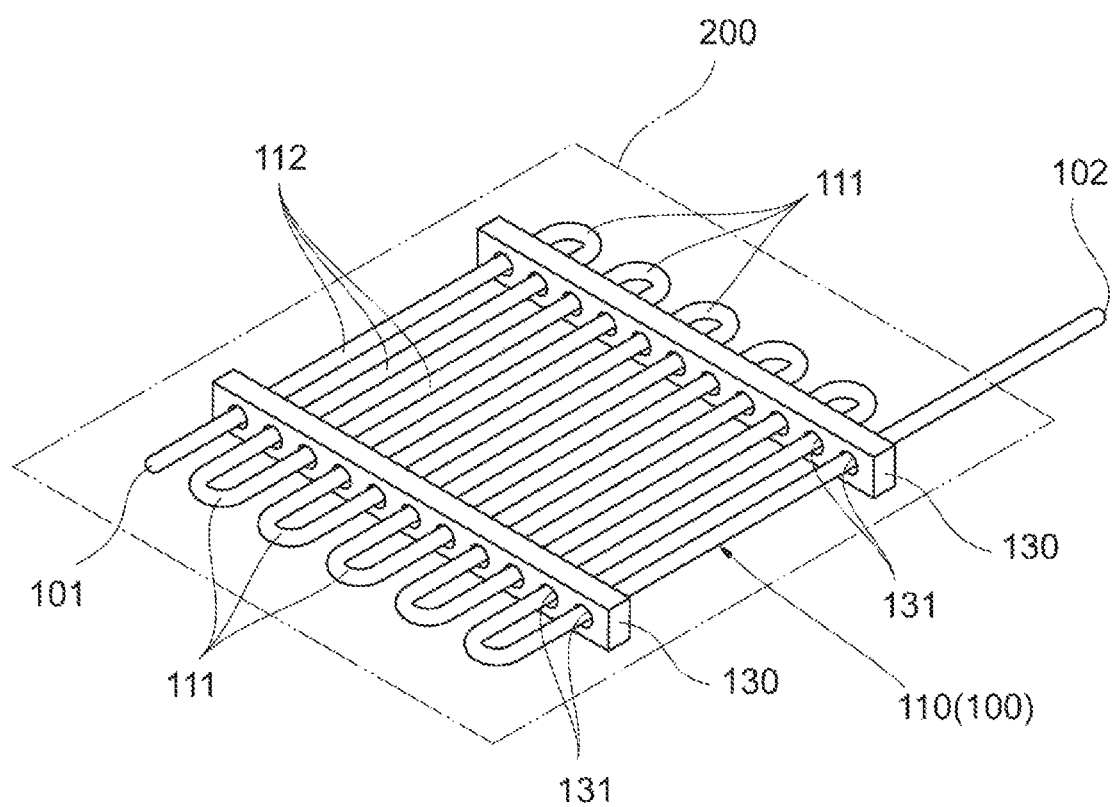
FIG. 3 is a diagram illustrating one example of the bag body.
Figure 4:
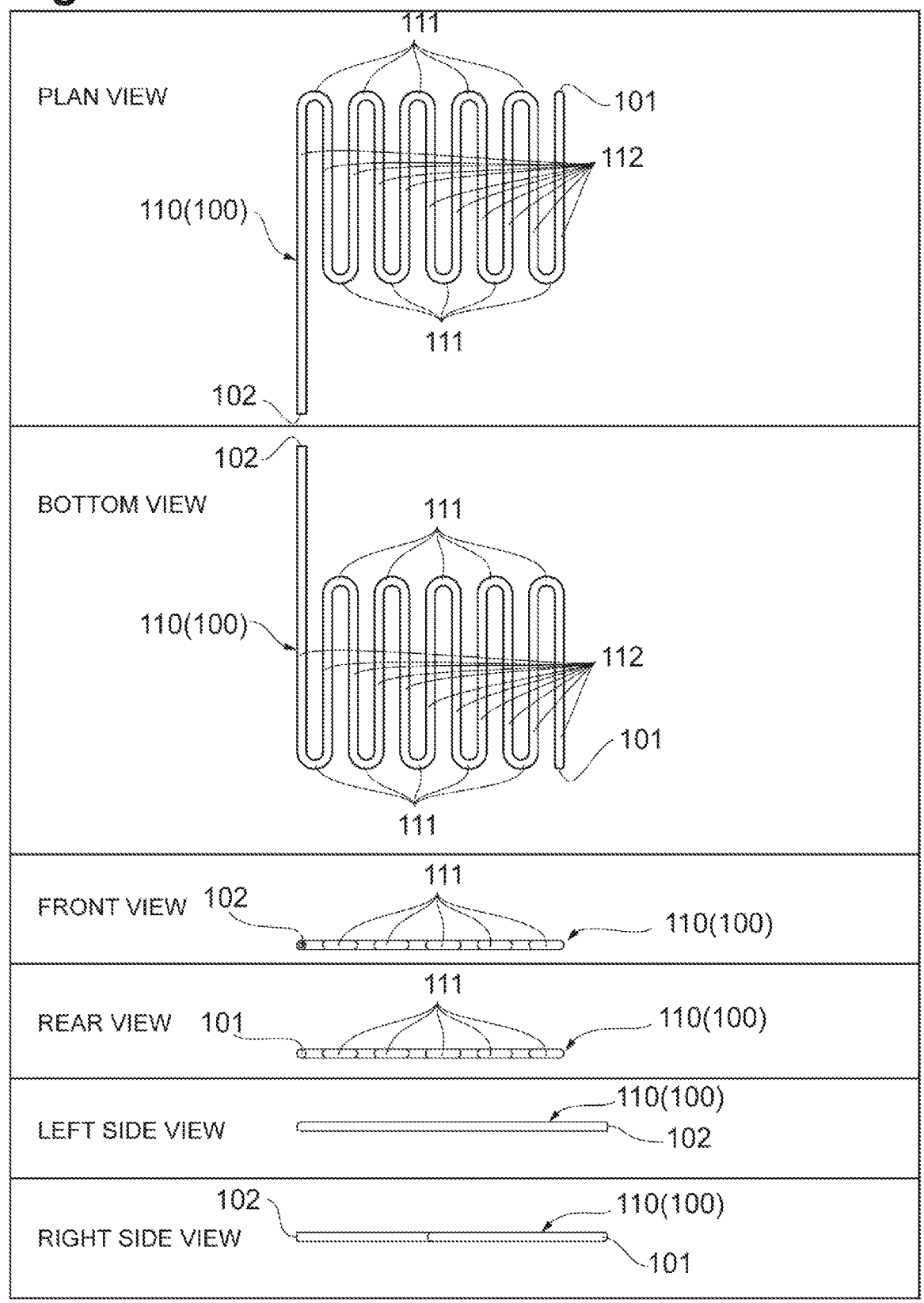
FIG. 4 includes six orthogonal views of the bag body depicted in FIG. 3.

FIGS. 1 to 4 illustrate an example in which the tubular portion 110 is arranged in a meandering manner on an imaginary plane. This tubular portion 110 has a plurality of curved portions 111 that are each bent substantially 180° into a U-shape, and the portions 112 thereof other than the curved portions 111 are arranged linearly. In the example of FIGS. 1 to 4, this meandering is regularly (orderly) formed. However, the form of the meandering is not limited to this example, and the tubular portion may meander randomly (disorderly). The expression "the tubular portion is arranged on an imaginary plane" means that the tubular portion is arranged on one imaginary plane 200 such that a plurality of portions of the tubular portion do not overlap each other as depicted in FIG. 3. The imaginary plane herein may be a flat plane or may be a curved plane. FIG. 4 includes six orthogonal views of the bag body 100 depicted in FIG. 3, and the configuration of the tubular portion 110 that is arranged in a meandering manner on the imaginary plane can be understood from these views.

In the present embodiment, the liquid bag 10 further includes a flat outer bag 120 configured to accommodate the bag body 100. This outer bag 120 also has flexibility. Examples of material of the outer bag 120 include polyolefin such as polyethylene (PE) and polypropylene (PP), polyester such as polyethylene terephthalate (PET), and halogenated polyolefin such as poly(vinylidene chloride) (PVDC). However, the material is not limited to particular one, and any material may be used if an outer bag 120 that can be easily bent can be made thereof. The outer bag 120 functions as a support portion that maintains the state in which at least part of the tubular portion 110 is bent, and further serves as a protector of the bag body 100. In FIGS. 1 and 2, the outer bag 120 is illustrated as a transparent bag, but the outer bag 120 may be semitransparent or may be opaque. A case configured to accommodate the bag body is not limited to this outer bag 120, and other types of cases may be used.

The structure of the support portion is not limited if bending of the tubular portion 110 can be maintained. For example, as depicted in FIG. 3, holders 130 each having a plurality of holes 131 formed therein through which the bag body (tubular portion 110) passes may be used as the support portion. The holder 130 suppresses an expansion of the tubular portion 110 in a radial direction of the tubular portion 110 and allows the tubular portion 110 to be extended in the axial direction of the tubular portion 130. Each holder 130 has a straight shape. However, the outer shape of the holder 130 is not limited to this. The holder 130 has flexibility. Examples of material of the holders 130 include silicone rubber, natural rubber, and synthetic rubber. However, the material is not limited to particular one, and any material may be used if the holders 130 that can be easily bent can be made thereof. Alternatively, a sheet or a tape having an adhesive layer may be used as the support portion. In this case, the bag body or the tubular portion is caused to adhere to the adhesive layer, whereby the bag body or the tubular portion is supported. Still alternatively, the tubular portion may be fixed or supported such that the shape thereof is maintained, by causing adjacent tubes to adhere to each other or bonding the adjacent tubes together. Still alternatively, a plurality of components may function as the support portion. For example, bending of the tubular portion 110 may be maintained by the outer bag 120 and the holder 130.

Figure 5:
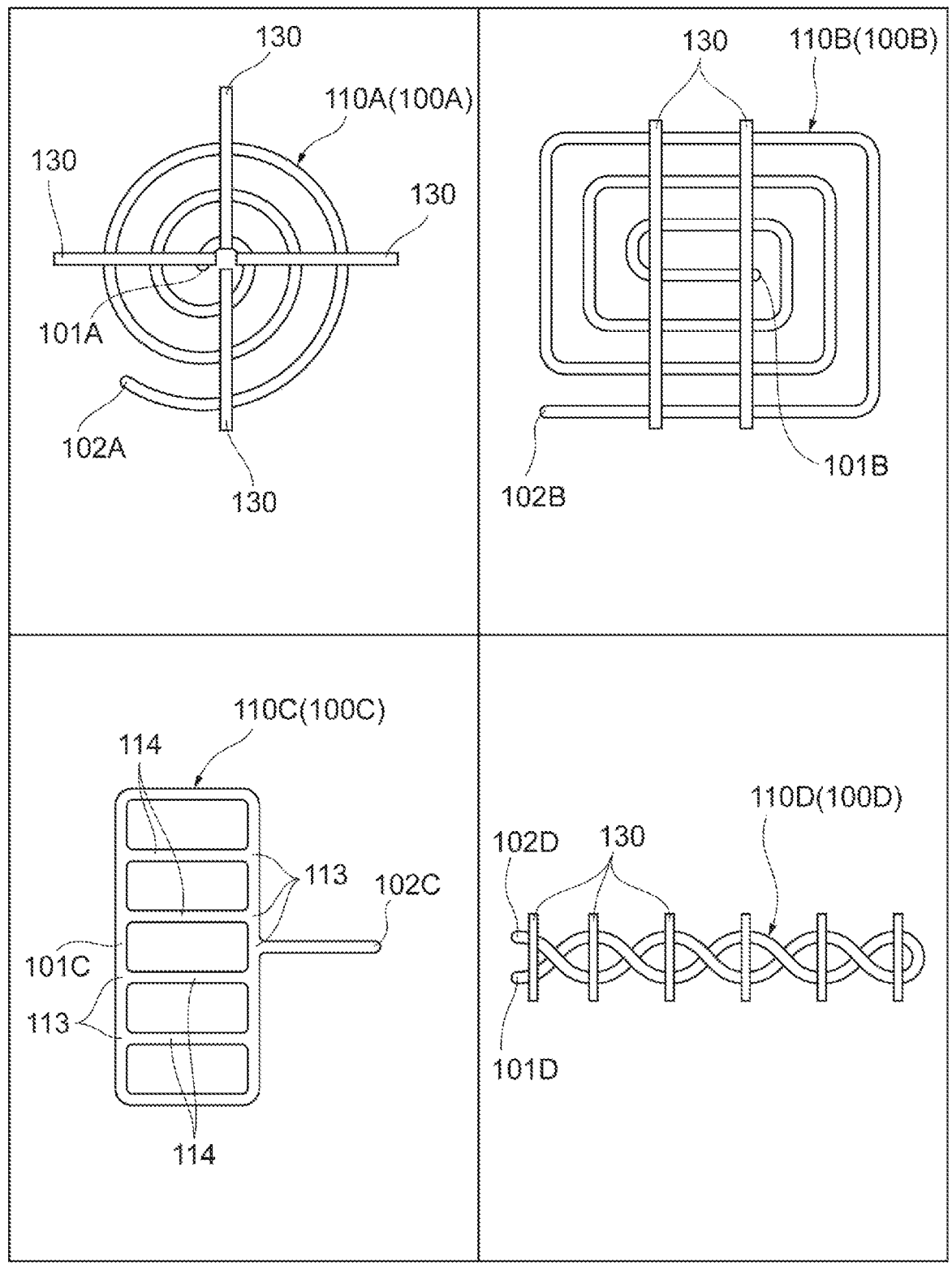
FIG. 5 includes diagrams illustrating various other examples of the bag body.

The form of bending of the tubular portion is not limited to the example of FIGS. 1 to 4, and any various forms may be used. Other examples of bending of the tubular portion are illustrated in FIG. 5, and every bag body has a tubular shape in these examples.

The bag body 100A has a bottom 101A, a port 102A, and a tubular portion 110A, and the tubular portion 110A is arranged, on an imaginary plane, in a spiral shape that is substantially circular. The bag body 100B has a bottom 101B, a port 102B, and a tubular portion 110B, and the tubular portion 110B is arranged, on an imaginary plane, in a spiral shape that is substantially rectangular. The spiral shape is not limited to these two examples, and may be formed in another shape such as a substantial triangle. In the bag bodies 100A and 100B, the tubular portions 110A and 110B are supported by holders 130 that are similar to those depicted in FIG. 3 such that the bending shapes thereof are maintained. However, as described above, other types of support portions may be used, or no support portion may be used.

The bag body 100C has a linear bottom 101C, a port 102C, and a tubular portion 110C. The tubular portion 110C, at least part of which is bent, is arranged on an imaginary plane. In this example, the tubular portion 110C has a plurality of branch portions 113. The number of the branch portions is not limited to a particular number, and may be one. For example, a form of the bag body 100C in which four portions 114 are omitted and a substantially rectangular flow passage is left will be a tubular portion having only one branch portion 113 that is closest to the port 102C. In the bag body 100C, no support portion is used. However, as described above, any type of support portions may be used for the bag body 100C.

The tubular portion does not necessarily have to be arranged on an imaginary plane. One example of this is a bag body 100D having a bottom 101D, a port 102D, and a tubular portion 110D. As depicted in FIG. 5, by twisting the tubular portion 110D, part of the tubular portion 110D and other part thereof may be overlapped. In the bag body 100D, the tubular portion nor) is supported by holders 130 that are similar to those depicted in FIG. 3 such that the bending shape thereof is maintained. However, as described above, other types of support portions may be used, or no support portion may be used.

As depicted in FIGS. 1 and 2, by flattening the liquid bag, a user can easily fix the liquid bag onto a living body when using the administration device, and consequently the portability of the liquid bag is enhanced. Such enhanced portability can be obtained also when various types of bag bodies depicted in FIG. 5 are used. The user may cause the liquid bag to adhere onto a living body when using the administration device. The expression "cause the liquid bag to adhere onto a living body" means a concept including both a form of causing the liquid bag to adhere onto his/her skin and a form of causing the liquid bag to adhere onto clothes that the user is wearing. The liquid bag may include an adhesive layer on any surface thereof so as to adhere onto a living body. When the liquid bag itself does not include an adhesive layer, the user may use an adhesive tape, for example, to cause the liquid bag to adhere onto a living body. As is understood, the user may use the administration device without causing the liquid bag to adhere onto a living body.

Figure 6:
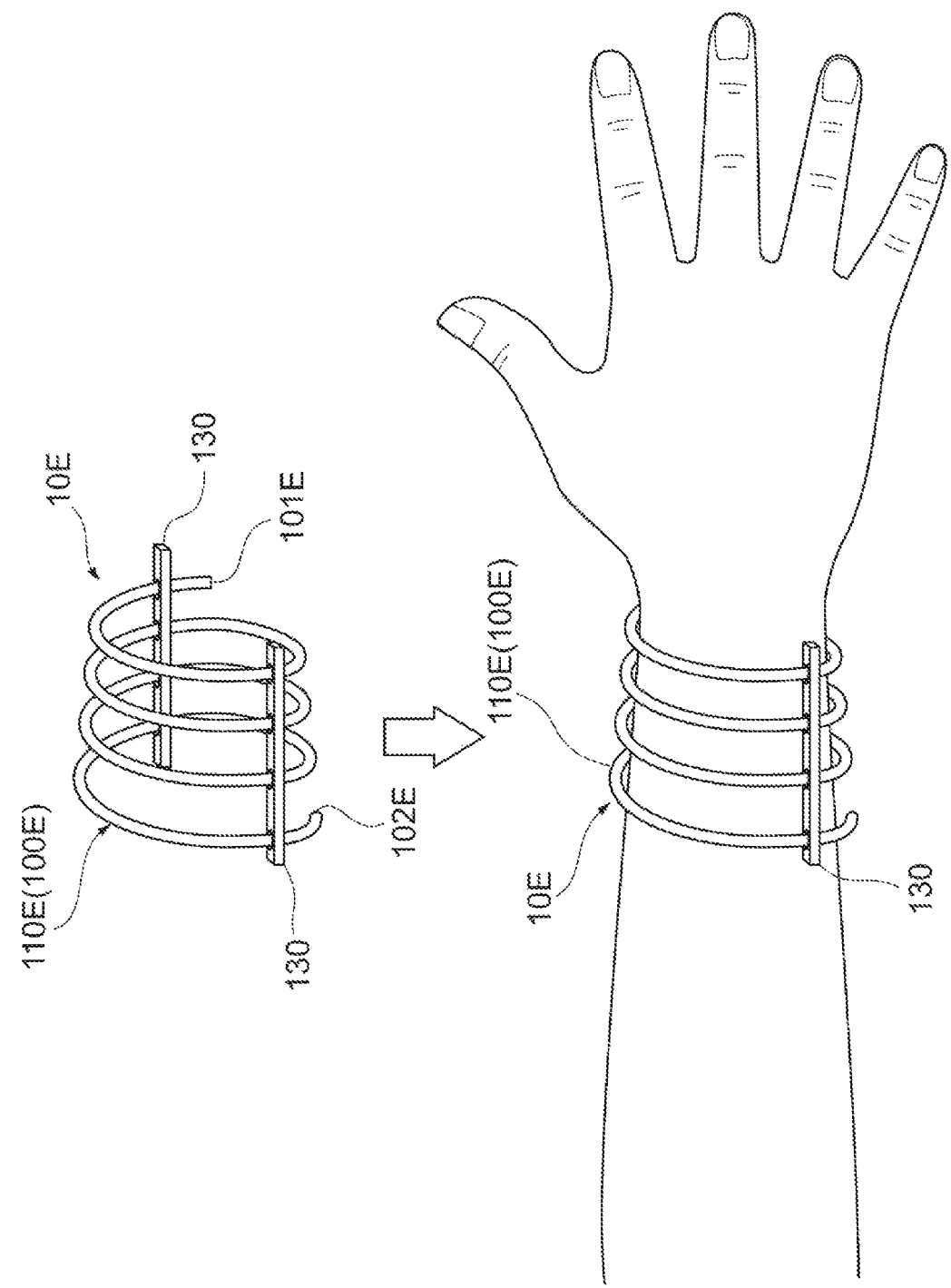
FIG. 6 is a diagram illustrating still another example of the liquid bag and an example of a situation in which this liquid bag is attached.

A liquid bag the entire area of which is thin can be made by a method other than flattening the liquid bag itself. For example, the liquid bag 10E depicted in FIG. 6 includes a bag body 100E, and the bag body 100E has a bottom 101E, a port 102E, and a tubular portion 110E that is helically arranged. The entire shape of this bag body 100E can be considered to be tubular. The liquid bag 10E further includes holders 130, but other types of support portions may be used, or no support portion may be used. As depicted in FIG. 6, the user can carry the liquid bag 10E by wrapping the tubular portion 110E (bag body 100E) around his/her body (e.g., aim or leg).

The arrangement of the tubular portion can be considered in various forms as depicted in the examples of FIGS. 1 to 6, but the arrangement is not limited to these examples. For example, two or more arrangements that are optionally selected from a plurality of arrangements depicted in the examples of FIGS. 1 to 6 may be combined. Thus, a tubular portion having both the meandering arrangement and the branch portions, a tubular portion having both the helical arrangement and the branch portions, a tubular portion having both the spiral arrangement and the helical arrangement, and the like can also be considered. The method of bending the tubular portion may be determined from any viewpoints of ease in producing the liquid bag and dimensions of the liquid bag, for example. For example, when the tubular portion is arranged in a regularly meandering manner as depicted in FIGS. 1 to 3, the distance between adjacent parts of the tubular portion can be easily grasped by estimating expansion of the tubular portion due to stored liquid. Furthermore, when the holders 130 are used as the support portion, the holders 130 can be easily arranged. As is understood, the forms depicted in FIG. 5 or FIG. 6 may be more advantageous from another viewpoint.

The dimensions (more specifically, inside diameter, outside diameter, total length, and thickness) of the tubular portion may be determined based on the amount of an active ingredient or liquid to be administered, or may be determined in consideration of portability of the liquid bag or the administration device. For example, by increasing the total length while reducing the outside diameter, and by bending at least part of the tubular portion with respect to the axial direction to confine the space occupied by the tubular portion within a limited area (e.g., within the area of the dimensions of the outer bag 120 depicted in FIGS. 1 and 2), a liquid bag that is excellent in portability can be provided.

Figure 7:
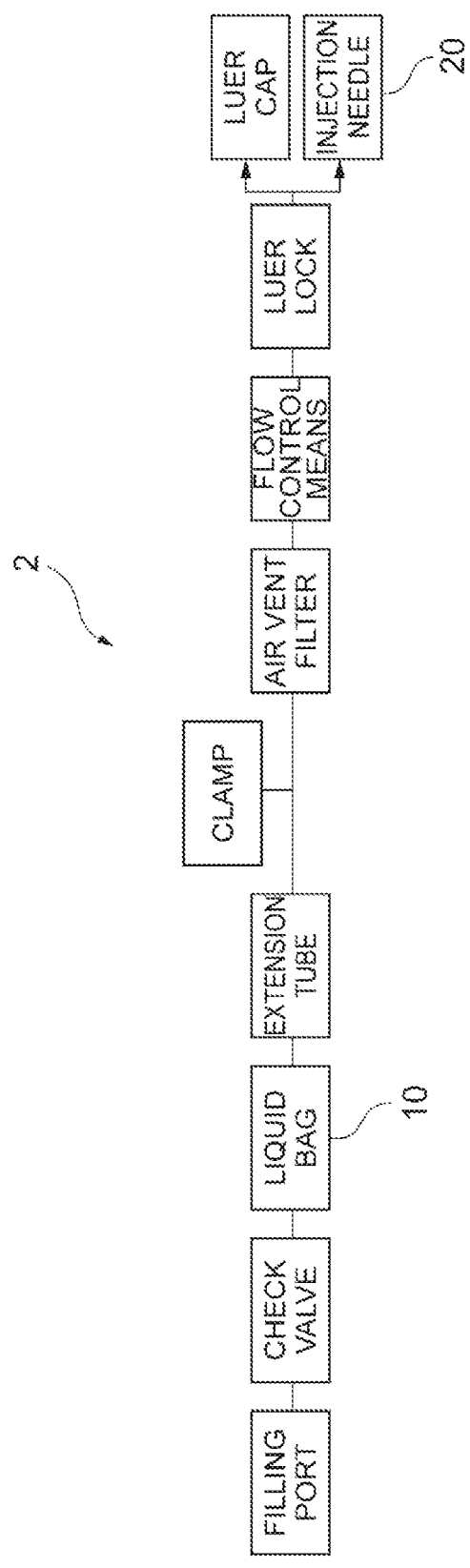
FIG. 7 is a block diagram illustrating one example of configuration of the administration device.
Figure 8:
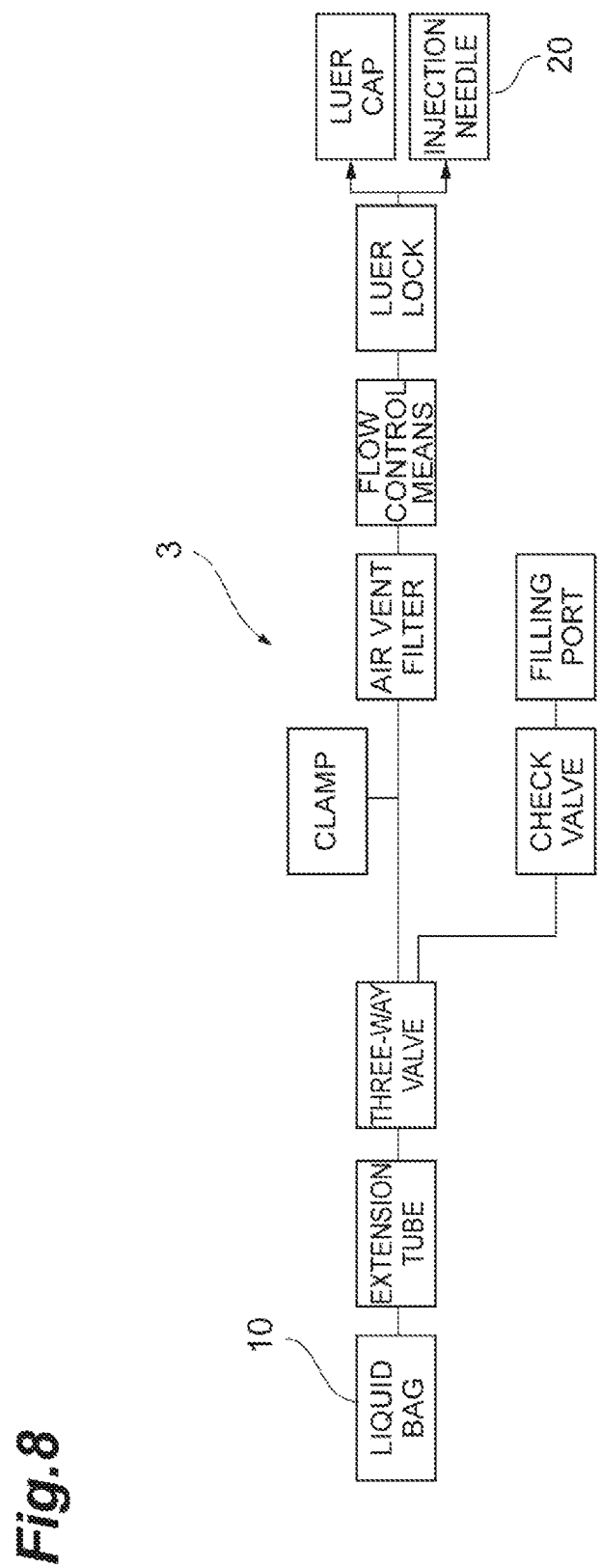
FIG. 8 is a block diagram illustrating another example of the configuration of the administration device.

The following describes usages of administration devices each including the liquid bag according to the present embodiment with reference to FIGS. 7 and 8. Both of Ms. 7 and 8 are block diagrams illustrating configurations of the administration devices each including the liquid bag. In each of these two diagrams, the liquid bag and an injection needle are designated by reference signs 10 and 20, respectively, for convenience.

Usage of the administration device 2 depicted in FIG. 7 is as follows. To begin with, a user charges a predetermined amount of liquid from a filling port with a Luer cap being attached to a Luer lock and with a clamp being closed, thereby filling the liquid bag 10 with the liquid. Subsequently, the user removes the Luer cap, attaches the injection needle 20 to the Luer lock, and loosens the clamp to allow the liquid to reach the injection needle 20, thereby purging air bubbles, and then closes the clamp.

Subsequently, the user fixes the administration device 2 to a living body, inserts the injection needle 20 into skin, and opens the clamp to administer the liquid (active ingredient) into the living body.

After the administration is completed, the user closes the clamp, pulls out the injection needle 20 from a vein, and detaches the administration device 2 from the living body.

Usage of the administration device 3 depicted in FIG. 8 is as follows. To begin with, a user attaches a Luer cap to a Luer lock, closes a clamp, and operates a three-way valve so as to cause the liquid bag 10 to communicate with a filling port. Subsequently, the user charges a predetermined amount of liquid from the filling port to fill the liquid bag 10 with the liquid, and then operates the three-way valve to close a flow passage from the filling port to the liquid bag 10.

Subsequently, the user removes the Luer cap, attaches the injection needle 20 to the Luer lock, and loosens the clamp to allow the liquid to reach the injection needle 20, thereby purging air bubbles, and then closes the clamp.

Subsequently, the user fixes the administration device 3 to a living body, inserts the injection needle 20 into skin, and opens the clamp to administer the liquid (active ingredient) into the living body. After the administration is completed, the user closes the clamp, pulls out the injection needle 20 from a vein, and detaches the administration device 3 from the living body.

As is understood, the configurations of the administration devices 2 and 3 described above are merely examples, and thus other configurations may be used. Accordingly, usages of the administration devices are not limited to these examples. For example, usage of the administration device 1 depicted in FIG. 1 may be different from those of the administration devices 2 and 3.

As described in the foregoing, the liquid bag according to one aspect of the present invention is a liquid bag for storing liquid containing an active ingredient to be transdermally administered, and includes a bag body configured to store the liquid and feed the liquid toward an injection needle. The bag body includes a tubular portion, and at least part of the tubular portion is bent with respect to the axial direction of the tubular portion with the liquid being stored in the tubular portion.

In this aspect, because at least part of the tubular portion storing the liquid is bent, the tubular portion having a longer length can be accommodated in a limited space. Thus, a larger amount of liquid can be stored within the limited space. Forming the bag body in this manner allows the space occupied by the bag body to be narrowed, and thus the portability of the liquid bag can be enhanced and the active ingredient in an amount needed for transdermal administration can be stored in the liquid bag. For example, a user can easily move while carrying the administration device and receiving administration of the active ingredient.

The liquid bag according to another aspect may further include a support portion configured to maintain a state in which the at least part of the tubular portion is bent. In this case, a state in which the tubular portion fits into a limited space can be maintained. Even after the tubular portion is expanded by charging liquid therein, this specific bent state of the tubular portion can be maintained. Furthermore, even in a stage in which the tubular portion gradually constricts while the liquid is being administered to a living body, the specific bent state of the tubular portion can be maintained.

In the liquid bag according to another aspect, the at least part of the tubular portion may be arranged in a spiral or meandering manner on an imaginary plane. In this case, the tubular portion having a long length can be efficiently accommodated in a limited space, and also the thickness of the liquid bag can be reduced. Consequently, the portability of the liquid bag can be further enhanced.

In the liquid bag according to another aspect, the at least part of the tubular portion may be helically arranged. In this case, the bag body can be attached to a living body so as to be wrapped around part (e.g., aim or leg) of the living body. This arrangement also serves as one method of enhancing the portability of the liquid bag.

In the liquid bag according to another aspect, the tubular portion may have a branch portion. In this case, the total length of the tubular portion in a limited space can be increased, and thus a larger amount of liquid can be stored in the limited space.

The present invention has been described above in detail based on the embodiment thereof. However, the present invention is not limited to the above-described embodiment. In the present invention, various modifications can be made within the scope not departing from the gist thereof.

In the embodiment, the tubular bag body has been described, but only part of the bag body may be a tubular portion. In this case, a portion other than the tubular portion may have any shape such as a plate-like shape, a rectangular parallelepiped shape, and a spherical shape. When only part of the bag body is a tubular portion, the tubular portion may be positioned anywhere in the bag body, and may be positioned at, for example, a portion including a bottom, a portion including a port, or a central portion that does not include the bottom or the port.

REFERENCE SIGNS LIST 1 to 3 . . . administration device, 10, 10E . . . liquid bag, 20 . . . injection needle, 30 . . . tube, 40 . . . clamp, 50 . . . filter, 100, 100A to 100E . . . bag body, 110, 110A to 110E . . . tubular portion, 111 . . . curved portion, 113 . . . branch portion, 120 . . . outer bag, 130 . . . holder

The invention claimed is:

1. A liquid bag for storing liquid containing an active ingredient to be transdermally administered, the liquid bag comprising:
   a bag body including a bottom, a tubular portion that is expanded or extended by a pressure of the liquid charged, and a port, and configured to retain the liquid and feed the liquid toward an injection needle, at least part of the tubular portion being bent with respect to an axial direction of the tubular portion with the liquid being retained in the tubular portion; and
   a holder having flexibility and a straight shape, and configured to maintain a state in which the at least part of the tubular portion is bent, and having a plurality of holes formed therein through which the tubular portion passes,
   wherein the state in which the at least part of the tubular portion is bent is maintained by the tubular portion passing through the plurality of holes in the holder, and
   wherein, when the bag body is filled with the liquid, the holder suppresses an expansion of the tubular portion in a radial direction of the tubular portion and allows the tubular portion to be extended in the axial direction of the tubular portion.

2. The liquid bag according to claim 1, wherein the at least part of the tubular portion is arranged in a spiral or meandering manner on an imaginary plane.

3. The liquid bag according to claim 1, wherein the at least part of the tubular portion is helically arranged.

4. The liquid bag according to claim 1, wherein the tubular portion has a branch portion.

* * * * *